United States Patent [19]

Harui

[11] Patent Number: 4,474,184
[45] Date of Patent: Oct. 2, 1984

[54] BUBBLE TRAP FOR ULTRASOUND SCANHEAD

[75] Inventor: Norio Harui, Seattle, Wash.

[73] Assignee: Advanced Technology Laboratories, Inc., Bellevue, Wash.

[21] Appl. No.: 423,923

[22] Filed: Sep. 27, 1982

[51] Int. Cl.³ .............................................. A61B 10/00
[52] U.S. Cl. ........................................ 128/660; 73/644
[58] Field of Search ......................... 128/660; 604/122; 73/644, 633

[56] References Cited

U.S. PATENT DOCUMENTS

| | | | |
|---|---|---|---|
| 2,002,008 | 5/1935 | Harris | 604/122 X |
| 3,343,538 | 9/1967 | Morley | 604/122 |
| 4,143,659 | 3/1949 | Biedermann | 604/251 |
| 4,316,271 | 2/1982 | Evert | 128/660 X |

Primary Examiner—Kyle L. Howell
Assistant Examiner—Deidre A. Foley
Attorney, Agent, or Firm—Lawrence S. Levinson; Sanford J. Asman

[57] ABSTRACT

A bubble trap for use with an ultrasonic scanhead is described. The bubble trap is comprised of a reservoir chamber connected to the main chamber housing the ultrasound transducer. The reservoir chamber is connected via a channel which extends from the main chamber to an orifice in the volumetric center of the reservoir chamber. Thus, any bubble which flows up through the orifice into the reservoir chamber will be trapped there, and will thereby be removed from the main chamber.

2 Claims, 6 Drawing Figures

BUBBLE TRAP FOR ULTRASOUND SCANHEAD

BACKGROUND OF THE INVENTION

The present invention relates to a bubble trap. It has particular application in devices in which the presence of bubbles has a deleterious effect, such devices include, but are not limited to, mechanical ultrasound devices, such as medical ultrasound scanners.

In ultrasonic devices that require an acoustic fluid transmission medium, it is essential that there be no gas bubbles in the path of the acoustic beam. Since some devices have sealed moving drive shafts, leakage through the seal invariably occurs. Consequently, bubbles form in the fluid. Even those devices that do not have dynamic seals can have bubbles due to the permeability of the housing material, typically a plastic. If the internal parts are made of plastic or epoxy, some outgassing within them may also occur, and such outgassing produces gas bubbles. Therefore, it is extremely difficult to keep such devices bubble free, and a convenient means for removing any bubbles present would be a very desirable feature.

SUMMARY OF THE INVENTION

In accordance with the present invention, a device which acts as a bubble trap in an ultrasound scanhead comprises a reservoir chamber which is intended to capture and contain any bubbles that may form in a main chamber which is to be kept bubble free. The reservoir chamber has a shape whereby bubbles may enter the reservoir chamber from the bubble free main chamber, but the shape is such that bubbles which enter the reservoir chamber cannot flow back into the bubble free main chamber. This is accomplished by locating the orifice between the two chambers such that it extends from the wall of the main chamber to the volumetric center of the reservoir chamber. Therefore, no matter what angle the device is tilted to, the orifice in the reservoir chamber is always below the fluid surface level.

DETAILED DESCRIPTION OF AN EXEMPLARY EMBODIMENT

Figure 1:
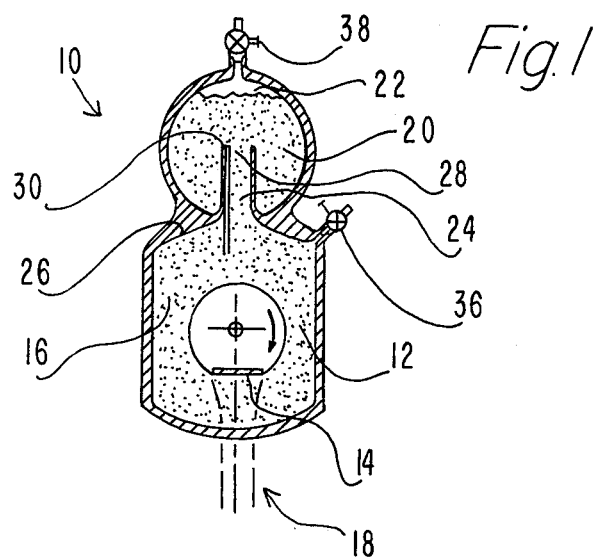
FIG. 1 is a side view of a portion of an ultrasound scanhead which employs the bubble trap of the present invention.

Referring generally to FIG. 1, the side view of a portion of an ultrasound mechanical sector scanner 10 employing the present invention, is shown. Only a portion of the ultrasound scanner unit 10 is shown as such units have heretofore been described and are commonly used. The portion of the ultrasound scanner unit 10 shown in FIG. 1 comprises a main chamber 12 which houses an ultrasound transducer 14. The transducer 14 may be either of the oscillating or rotating type without altering the present invention.

The transducer 14 is contained within the main chamber 12 which has an acoustical coupling fluid 16, such as mineral oil, which must be kept free of bubbles in order that the sound beam 18 emanating from the transducer 14 is unaffected thereby. In accordance with the present invention, a reservoir chamber 20 is formed adjacent to the main chamber 12. The reservoir chamber 20 is out of the acoustic path 18 of sound which leaves or returns to the transducer 14. Accordingly, the reservoir chamber 20 may contain trapped gas 22, as shown in FIG. 1. Such trapped gas 22 will not affect the operation of the ultrasound unit 10, so long as it is kept out of the acoustic path 18 from the transducer 14 in the manner shown. The main chamber 12 and the reservoir chamber 20 are connected together via a channel 24 which extends from a wall 26 of the main chamber 12 to an orifice 28 in the volumetric center of the reservoir chamber 20. The channel 24 permits the free flow of bubbles from the main chamber 12 into the reservoir chamber 20.

As will be seen hereafter trapped gas 22 within the reservoir chamber 20 cannot pass back through the orifice 28 into the main chamber 12 due to the geometry of the bubble trap. The device 10 further comprises a vent apparatus, such as the vent tube 30, shown in FIG. 1. In an alternative embodiment of the invention vent grooves 32 shown in FIG. 3 may be used instead of the vent tube 30.

With reference to FIG. 1, when a bubble appears in the main chamber 12, the bubble will pass through the channel 24 and out the orifice 28 into the reservoir chamber 20 when the device 10 is oriented in a manner such that the bubble can pass upward through the channel 24. Once a bubble has passed through the orifice 28 into the reservoir chamber 20, the bubble can no longer flow back through the channel 24 into the main chamber 12 if the orifice 28 is at the volumetric center of the reservoir chamber 20.

Figure 2A:
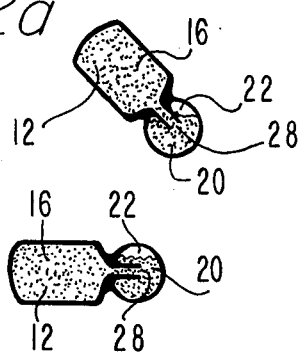
FIGS. 2A, 2B, 2C, and 2D are side views of the device of FIG. 1 in various orientations with the ultrasound transducer and vent tube removed for clarity.
Figure 2B:
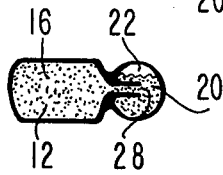
Figure 2D:
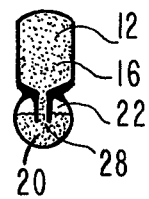
Figure 2C:
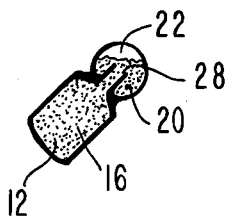

With reference to FIGS. 2A–2D, the fact that the surface of the trapped gas 22 is always above the orifice 28 in the reservoir chamber 20 is readily illustrated. Thus, whether the main chamber 12 is tilted up, as shown in FIG. 2A; or on its side, as shown in FIG. 2B; or tilted down, as shown in FIG. 2C; or upside down, as shown in FIG. 2D, it remains impossible for any of the trapped gas 22 to enter the orifice 28 and pass back through the channel 24 into the main chamber 12.

Figure 3:
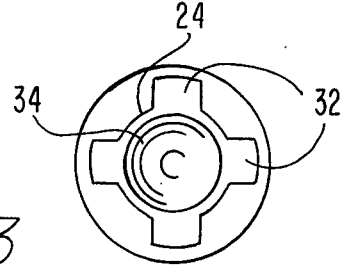
FIG. 3 is an enlarged end view of an orifice between the main chamber and the reservoir chamber in an alternative embodiment of the invention.

As will be recognized by those skilled in the art, any bubble which is larger than the diameter of the channel 24 cannot flow from the main chamber 12 into the reservoir chamber 20 without a vent, since the bubble may itself block the orifice 28 and not allow fluid 16 to pass into the main chamber 12 from the reservoir chamber 20. Accordingly, either a vent tube 30 (as shown in FIG. 1) or vent grooves 32 (as shown in FIG. 3) must be used in order to permit the flow of bubbles 34 as large as, or larger than the diameter of the channel 24 or the orifice 28. The vent passages, whether of the type shown in FIG. 1 or of the type shown in FIG. 3, allow fluid 16 to flow freely from the reservoir chamber 20 into the main chamber 12 in order to displace the volume of fluid 16 that was previously occupied by the bubble 34 in the main chamber 12. In other words, the vent pressure equalizes the pressures in the chambers 12, 20 and allows bubbles to pass through the channel 24 by their own buoyant force.

When the level of the fluid 16 in the reservoir chamber 20 approaches the level of the orifice 28, the device 10 requires refilling. In order to reduce the service interval, the reservoir chamber 20 should be made as large as possible and the vent 30 and orifice 28 should be as small as practical to maximize the volume of the reservoir chamber 20 above the orifice 28 and vent 30 at all orientation angles.

In order to introduce fluid 16 into the main chamber 12, a fill port 36 is used. When the fill port is opened, a vent port 38 is also opened to permit some trapped gas 22 to leave the reservoir chamber 20.

An additional feature inherent in the present invention is that a small amount of gas 22 can be intentionally trapped in the reservoir chamber 20. Such trapped gas 22 serves as an expansion and contraction compensator as the trapped gas 22 can expand and contract, while the fluid 16 within the chambers 12, 20 cannot do so.

I claim:

1. An improved bubble trap for an ultrasound transducer of the type comprising:
   (a) a main housing body portion defining a chamber in which the ultrasound transducer is mounted, said body portion having a wall member; and
   (b) an access port in said wall member through which fluid fill may be admitted to said chamber and through which gases in said chamber may be purged, said access port including means defining a bubble trap cavity;
   wherein the improvement comprises at least one vent groove formed in said access port between said chamber and said cavity whereby gases can pass through said access port in one direction while fluid passes through said vent groove in the opposite direction.

2. The improved bubble trap for an ultrasound scanhead of claim 1 further comprising a tube which extends into said cavity from said access port, the end of said tube which is located in said cavity being more distant from said chamber than the volumetric center of said cavity, whereby in any orientation, a maximum amount of gas can be collected from said chamber in said cavity before it is possible for gas to flow back through said opening into said chamber.

* * * * *